United States Patent [19]
Franseen et al.

[11] Patent Number: 5,362,232
[45] Date of Patent: * Nov. 8, 1994

[54] ORTHODONTIC APPLIANCE MOUNTING BASE

[75] Inventors: Steven A. Franseen, Denver; Jeffrey A. Peterson, Aurora, both of Colo.

[73] Assignee: RMO, Inc., Denver, Colo.

[*] Notice: The portion of the term of this patent subsequent to Oct. 27, 2009 has been disclaimed.

[21] Appl. No.: 967,200

[22] Filed: Oct. 27, 1992

Related U.S. Application Data

[63] Continuation of Ser. No. 649,594, Feb. 1, 1991, Pat. No. 5,158,452.

[51] Int. Cl.⁵ .................................................. A61C 3/00
[52] U.S. Cl. ........................................................ 433/9
[58] Field of Search ............................ 433/4, 8, 9, 24

[56] References Cited

U.S. PATENT DOCUMENTS

| | | | |
|---|---|---|---|
| D. 290,040 | 5/1987 | Kelly | D24/16 |
| 3,969,821 | 7/1976 | Lee, Jr. et al. | 433/9 |
| 4,063,360 | 12/1977 | Waller | 32/14 |
| 4,165,561 | 8/1979 | Miller et al. | 433/9 |
| 4,219,617 | 8/1980 | Wallshein | 433/9 |
| 4,243,386 | 1/1981 | Kawaguchi | 433/9 |
| 4,544,353 | 10/1985 | Maurer et al. | 433/9 |
| 4,604,057 | 8/1986 | Viglietti | 433/9 |
| 4,659,309 | 4/1987 | Merkel | 433/9 |
| 4,661,059 | 4/1987 | Kanno | 433/9 |
| 4,735,569 | 4/1988 | Munk | 433/9 |
| 4,838,786 | 6/1989 | Reher et al. | 433/9 |
| 4,902,224 | 2/1990 | Collins et al. | 433/8 |
| 4,936,773 | 6/1990 | Kawaguchi | 433/9 |
| 5,098,288 | 3/1992 | Kesling | 433/9 |

FOREIGN PATENT DOCUMENTS

| | | | |
|---|---|---|---|
| 2534368 | 2/1977 | Germany | 433/9 |
| 2903768 | 8/1980 | Germany | 433/8 |

OTHER PUBLICATIONS

1983 Rocky Mountain Orthodontics Catalog, pp. 27 and 28.
Ortho Organizers, Inc., Advertisement "SUPREME Mini-Twin".

*Primary Examiner*—John J. Wilson
*Attorney, Agent, or Firm*—Sheridan Ross & McIntosh

[57] ABSTRACT

Rails (38) project from a mesial edge (40) and a distal edge (42) of a base (28) of an orthodontic appliance (30) forming a gap between the base (28) and a surface (32) of a tooth (34). At least one post (44) projects from the base (28) between the rails (38). The rails (38) and post (44) are dimensioned to substantially preclude post-/tooth contact and reduce the likelihood of appliance detachment from a curved tooth surface. The posts (44) are formed to resist shear forces associated with mastication and to facilitate the smooth flow of bonding material about the posts (44) when the base (28) is pressed against a tooth surface (32) during bonding.

3 Claims, 2 Drawing Sheets

ORTHODONTIC APPLIANCE MOUNTING BASE

This is a continuation of Ser. No. 649,594 filed Feb. 1, 1991, now U.S. Pat. No. 5,158,452, issued Oct. 27, 1992.

TECHNICAL FIELD OF THE INVENTION

This invention relates in general to orthodontic appliances, and in particular to mounting bases for attaching orthodontic appliances to the surface of a tooth.

BACKGROUND OF THE INVENTION

Orthodontic appliances are often attached to a labial or lingual tooth surface by using a bonding material such as cement which is rigid upon setting. Typically, in one step of the attachment process, the appliance base is coated with bonding material and then the base is pressed against a tooth surface. It is desirable, of course, that the resulting bond be strong enough to withstand forces exerted on the appliance during treatment. However, as is well known, failure of any device first occurs at the weakest point, and in the application of orthodontic devices to the surface of a tooth, the weakest point will be in the bond by design. As is well known, orthodontic adhesives are specifically tailored to provide this weakest point for the controlled debonding at the end of treatment. However, the problem typically is to select an adhesive having adequate strength for treatment that will still allow removal of the bracket at the end of treatment without causing damage to the tooth.

While there are many forces that act on the appliance, the resulting tensile/compressive forces are of interest herein. Due to the curvature, both mesio-distally and occlusal-gingivally, of tooth surfaces, many prior appliances have been susceptible to stress on the bond from tensile/compressive forces which may ultimately cause the bond to break resulting in appliance detachment. For example, a compressive force along one edge of the appliance will be transmitted directly to the bond. If there is a pivot point between the opposite edges of the appliance due to tooth curvature or other surface incongruities, the compressive force on the one edge may cause the tensile force on the bond near the opposite edge to be so great as to detach the appliance. Therefore, any place where support to resist a force is provided by the bond rather than part of the base, a failure is more likely to occur. In order to reattach the appliance, an unnecessary visit to the orthodontist is required and treatment is interrupted.

A specific example of this problem with tensile/compressive forces is illustrated by the tendency of an appliance to detach when a patient bites into a resistive food and masticatory forces are applied to the appliance. The masticatory forces tend to compress the bond near one edge of the base and tension the bond near the other edge. The resulting shear forces on the bond may cause the appliance to peel away from the tooth surface beginning at the edge in tension.

Another problem with known mounting bases is a tendency for air pockets to remain in the bonding material after application. Many known appliance bases are fabricated to include holes or recesses and/or for use with meshes in attempts to increase the bonding surface area of the appliance. However, it is difficult to apply the bonding material to expel air pockets adjacent to such surfaces in many appliances. For example, when pressed against a tooth surface, these base designs do not accommodate air pocket evacuation responsive to the compressive forces communicated through the bonding material due to a lack of open channels for the air and the bonding material to flow.

Orthodontists are typically concerned about the "seating" of the appliance on the tooth. Thus there is a tendency to give the appliance one more push after positioning the appliance on the tooth with adhesive after, the adhesive has started to "set" or polymerize. This tendency may cause the base to "rock" and create a weaker bond. Any rocking after polymerization of the adhesive has begun is likely to be detrimental to the overall strength and consistency of the bond.

Additionally, when using ceramic appliances there is a problem with breakage during removal of the appliance after treatment. Any broken parts are possible hazards to the patient and must be carefully removed whether loose in the mouth or stuck on the tooth. Any portions remaining on the tooth surface are especially troublesome as they must be ground off with a diamond burr which may result in damage to the surface of the tooth.

Thus, there is a need for an improved orthodontic appliance base which is stable on tooth surfaces of various curvatures thereby reducing the likelihood of separation therefrom and the resulting appliance failure. In addition, there is a need for an orthodontic appliance base which provides greater resistance to masticatory forces. There is also a need for an orthodontic appliance base which provides a large bonding surface area while reducing the likelihood that air pockets will remain between the bonding material and the base upon application to a tooth.

SUMMARY OF THE INVENTION

The present invention comprises an orthodontic appliance base which substantially reduces problems with prior bases. The inventive base is designed to accommodate bracket stability on a variety of tooth morphologists. In addition, the present invention provides bonding surfaces oriented relative to the occlusal plane to yield increased resistance to masticatory forces. The present invention is further designed to permit bonding material to spread relatively evenly and evacuate air pockets throughout the base/bonding material interface when the appliance is coated with bonding material and pressed against a tooth surface, thus reducing the likelihood of detachment.

In accordance with one aspect of the present invention, an orthodontic appliance base is provided with one or more offset posts projecting therefrom. Preferably, the posts comprise side portions oriented such that tangents thereto are transverse to the lateral and longitudinal axes of the base. In other words, such side portions are, upon application of the base to a tooth, neither parallel nor perpendicular to the gingivally directed masticatory forces. Consequently, the bond shear strength of the appliance is increased by reducing the likelihood of the formation of shear planes.

In accordance with another aspect of the invention, an orthodontic appliance base is provided having slightly arcuate (to accommodate the occlusal-gingival curvature of the tooth) side rails along the mesial and distal edges thereof which project a preselected distance, which is preferably beyond, the aforementioned posts in order to reduce appliance/tooth contact. Thus upon removal of the appliance after treatment, there is less likelihood of portions of the appliance breaking and remaining stuck to the surface of the tooth. In addition, the rails define borders which restrict bonding material flow upon application and tend to cause excess material to flow occlusal-gingivally when the base is pressed against a tooth surface, thereby evacuating air pockets. As will be further appreciated, the noted posts define interconnecting channels which accommodate such evacuation.

In one embodiment, the orthodontic appliance base comprises mesial and distal side rails and a plurality of offset posts positioned intermediate the rails. The rails are slightly arcuate occlusal-gingivally to conform to the typical occlusal-gingival tooth curvature. The rails protrude from the base toward the tooth surface a greater distance than any other portion of the base.

The posts are offset both laterally and longitudinally to reduce the likelihood of formation of a shear plane. Additionally, the posts have side portions formed at an angle, preferably 45°, to the lateral and longitudinal axes of the base. Thus, when bonding material is applied to base and the base is applied to the tooth, channels are available for the excess material to flow through. By providing channels for the bonding material to flow through, the likelihood that air will be trapped between the base and the bonding material is reduced.

The posts provide greater bonding surface area both parallel and perpendicular to forces acting on the appliance and form flow channels in combination with the side rails. The side rails serve to transmit force on the appliance directly to the tooth rather than the bonding material. Therefore, due to the present invention, premature detachment of the base is less likely to occur than with prior art devices.

The combination of the side rails and the posts provide an appliance that is better able to resist forces in the mouth during treatment. Once treatment is over and removal is required, the present invention accommodates removal of the appliance with reduced likelihood of damage to the tooth surface. Since the rails are the only portions of the appliance that directly contact the tooth surface, any breakage of the appliance will likely result in no pieces thereof remaining directly on the tooth surface, i.e., any broken pieces would likely be separated from the tooth surface by the bonding material.

BRIEF DESCRIPTION OF THE DRAWINGS

For a more complete understanding of the invention and for further advantages thereof, reference is now made to the following Detailed Description taken in conjunction with the accompanying Drawings, in which.

DETAILED DESCRIPTION OF THE INVENTION

Figure 1:
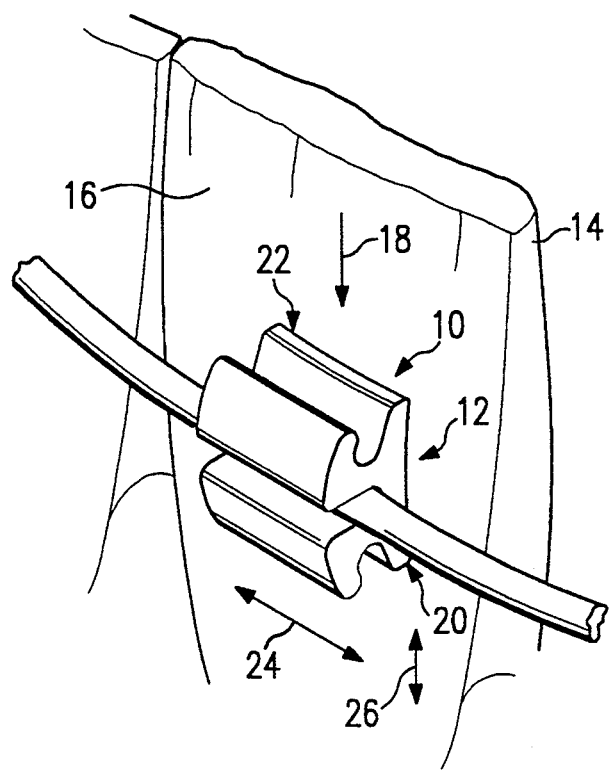
FIG. 1 is a perspective view of a prior art bracket attached to a tooth surface.

Referring first to FIG. 1, a prior art orthodontic bracket is generally identified by the reference numeral 12. The bracket 12 is attached to a tooth 14 by applying bonding material such as cement therebetween and pressing the bracket base 10 against a tooth surface 16. The resulting bond needs to be strong enough to withstand shear such as is associated with gingivally directed masticatory forces, represented by an arrow 18, exerted on the bracket 12 upon chewing. The masticatory forces 18 result in compression of the bond interface along a gingival region 20 of the base 10 and tension of the bonding interface along an occlusal region 22 thereof, and may cause the bracket 12 to peel off the tooth surface 16.

other conditions can also destroy the bond resulting in detachment of the bracket 12. First, because the tooth surface 16 is curved along both a mesio-distal axis 24 and along an occlusal-gingival axis 26, the base 10 of the bracket 12 is arcuately shaped to generally match the tooth surface 16. However, since there are many different shapes of teeth, it is difficult to produce the base 10, using modern economical mass production techniques, that will match every tooth shape. Thus, one must either settle for a finite number of base shapes that cover some workable percentage of teeth or individually custom design a base for every tooth. Since custom designing is generally not feasible, one must settle for a finite number of shapes and attempt to match the tooth as closely as possible. Any mismatch between the base 10 and the tooth 14 creates a potential pivot point about which compressive and tensile forces are transmitted to the cement from the bracket 12. Thus, failure is more likely due to base/tooth mismatch. Additionally, due to the orthodontist's tendency to give the bracket one more push during the polymerization process, pivot points may cause the bracket to rock and thus weaken the overall bond.

Second, air pockets may exist between the cement and the base 10 due to uneven cement application or surface discontinuities thereon. When the bracket 12 is pressed onto the tooth 14, air may not be able to escape, thus weakening the bond by reducing the bonding surface area where polymerization occurs and by creating faults in the cement which are prone to collapse under pressure. These conditions may result in bond failure and detachment of the bracket 10 when masticatory forces 18 are exerted thereon.

Figure 2:
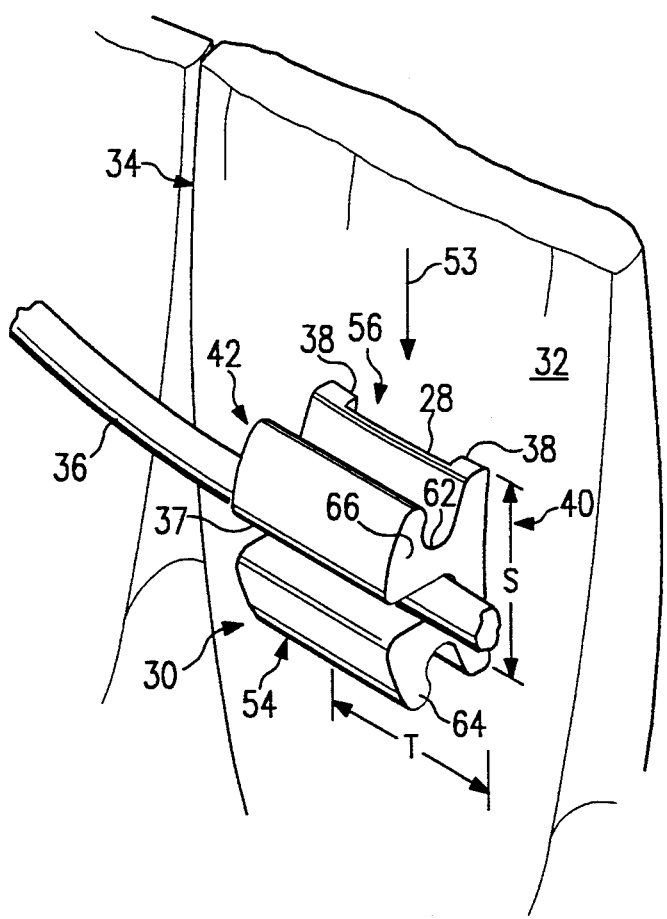
FIG. 2 is a perspective view of an orthodontic appliance, having a base formed in accordance with an embodiment of the present invention, attached to a tooth surface.
Figure 3:
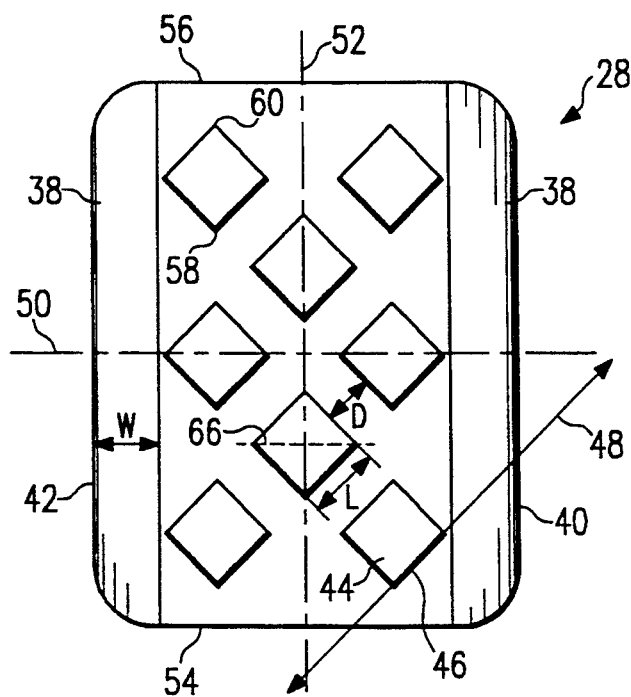
FIG. 3 is a bottom plan view of an orthodontic appliance having a base formed in accordance with the present invention.

In FIGS. 2-4, like items are identified by like and corresponding numerals for ease of reference. Referring first to FIG. 2, a perspective view of an appliance, having a base 28 formed in accordance with an embodiment of the present invention, is generally identified by the reference numeral 30. The appliance 30 comprises, for example, bondable lingual retainers, orthodontic brackets such as edgewise brackets (shown), light wire brackets, buccal tubes, and etc., having the base 28 for attachment to a surface 32 of a tooth 34. The appliance 30 is adapted to receive an archwire 36 in a slot 37 to apply corrective forces to the tooth 34. The appliance 30 may comprise any suitable material such as stainless steel, ceramic, plastic or a composite material.

The appliance 30 has an at least slightly arcuate mesial edge 40, an at least slightly arcuate distal edge 42, an at least slightly arcuate occlusal edge 56, and an at least slightly arcuate gingival edge 54. For example, the mesial and distal edges 40–42 may have a radius of curvature of approximately 0.433 inches over a length of 0.140 inches and the occlusal and gingival edges 56–54 may have a radius of curvature of approximately 0.140 inches over a width of 0.120 inches. The radius of curvature for each edge is selected to accommodate a range of teeth for which the base is designed.

As shown in FIG. 2, the appliance 30 is fixed to the surface 32 which is the labial surface of the tooth 34, however, it is to be understood that the appliance 30 may also be applied to the lingual surface of the tooth 34. The appliance 30 has a pedestal 62 which is integrally fixed to the base 28. A pair of wing tips 64 and 66 protrude from the pedestal 62. As is well known in the art, a retaining device such as, for example, a ligature wire (not shown) is attached around the wing tips 64 and 66 to retain the wire 36 in the slot 37.

Referring to FIG. 3, a bottom plan view of the appliance 10 is illustrated. The base 28 includes rails 38 projecting from the mesial edge 40 and the distal edge 42 thereof and at least one post 44 projecting therefrom. The rails 38 are positioned on the mesial edge 40 and the distal edge 42 because the occlusal-gingival curvature of a tooth is generally less from tooth to tooth than is the mesio-distal curvature. Thus the appliance 10 will be adapted for use on a wider variety of teeth. The posts 44 are arranged in an offset pattern along both a lateral axis 50 and a longitudinal axis 52 of the base 28 to reduce the likelihood of the formation of a shear plane. The post 44 has side portions 46 oriented such that a tangent 48 thereto is transverse to the lateral axis 50 and the longitudinal axis 52. The post 44 provides increased bonding surface area both perpendicular and parallel to forces acting on the appliance 10.

Although the illustrated posts 44 are substantially diamond shaped and are inclined approximately 45° relative to the lateral axis 50 of the base 28, it is to be understood that other shapes such as circles, ellipses, polygons, rhomboids or stars could be utilized. Similarly, other post orientations could be utilized. However, posts 44 that are offset and have side portions 46 which are not perpendicular to the gingivally directed masticatory forces indicated on FIG. 2 by an arrow 53 are more likely to resist failure. The posts 44 have, for example, a side length L of approximately 0.010 inches and a minimum distance D between adjacent posts of approximately 0.010 inches.

Figure 4A:
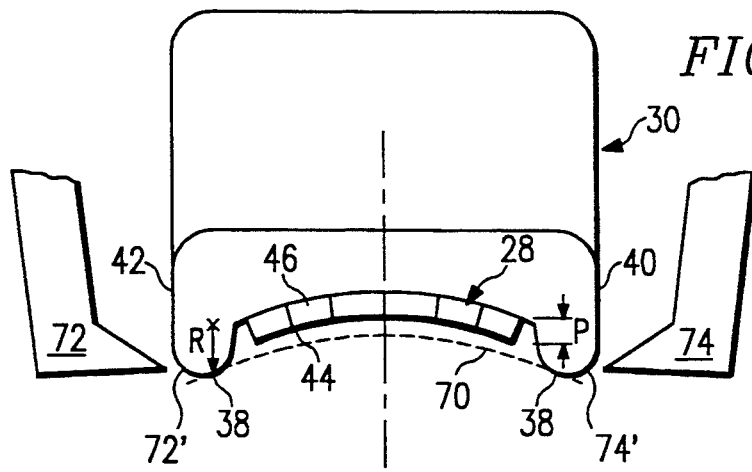
FIGS. 4A and 4B are front (occlusal) elevational view of an orthodontic appliance having a base formed in accordance with the present invention.
Figure 4B:
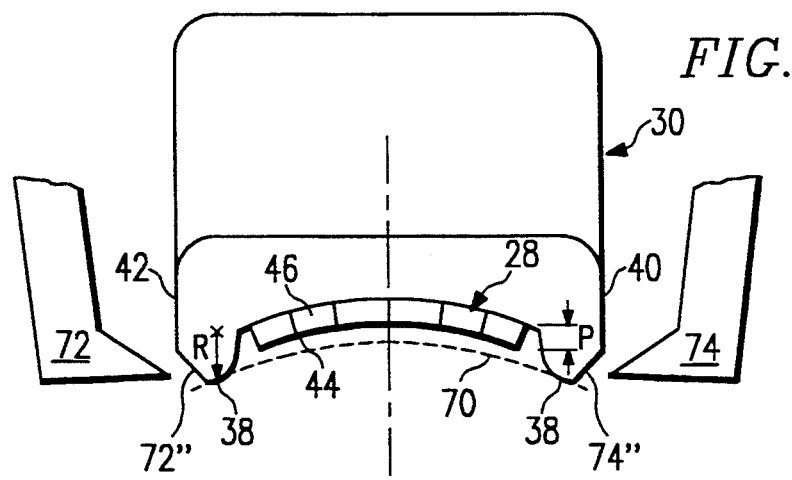

Referring to FIGS. 4A and 4B, an occlusally oriented elevational view of the appliance 30 is illustrated. In an important aspect of the present invention, the rails 38 extend a distance R from the base 28 which is greater than a distance P of the posts 44, thereby substantially precluding post/tooth contact and reducing the likelihood of forming pivot points therebetween. The rails 38 and posts 44 can be dimensioned to generally accommodate the curvature of the tooth surface 32 (see FIG. 2) for which the appliance 30 is designed. In one embodiment, the rails 38 extend the distance R which may be, for example, approximately 0.012 inches and the posts 44 extend the distance P which may be, for example, approximately 0.008 inches. The rails 38 may have a width W (see FIG. 3) of approximately 0.015 inches and, in an important aspect of the present invention, form purchase points which may comprise, for example, rounded edges (see FIG. 4A) or chamfered edges (see FIG. 4B) to facilitate removal when treatment is finished.

Due to the formation of purchase points 72', 74' and 72", 74", it is possible to insert a debonding tool between the surface of the tooth, as indicated by dashed line 70, and the rails 38. In FIG. 4A, the beaks 72 and 74 of a debonding plier, such as is available, for example, from ETM Corporation, are shown about to be used to remove the appliance 30. In comparison to prior art bases, the appliance 30 and the rails 38 will direct debonding forces away from the surface of the tooth by forming the purchase points 72', 74' and 72", 74", for engagement by the beaks 72 and 74 of the debonding plier. In prior appliances, removal attempts (after completion of treatment) may result in breaking of the appliance (especially if the appliance comprises ceramic) rather than separation from the tooth thus leaving jagged edges on the tooth. Any remaining portions of the appliance must then be ground off risking the possibility of damage to the tooth. With the present invention, even if the appliance 30 should break, the force of the beaks 72 and 74 of the debonding plier would lift the pieces up and away from the surface of the tooth 70. In this regard, as can be seen in FIGS. 4A and 4B, the beaks 72, 74 of the debonding pliers are positioned under the respective purchase points 72', 74' and 72", 74", and thus under the base 28, before a force is exerted on the base 28 by the debonding tool. Specifically, the effective angle of the purchase points 72', 74' and 72" and 74" facilitates the positioning of the debonding pliers under the base 28 prior to forcible engagement with the base 28. Additionally, since the only portion of the appliance 30 touching the tooth is the rails 38, there is less material that could remain on the tooth after debonding (should fracture of the appliance occur).

The rails 38 also serve to contain the cement when the base 28 is pressed against the tooth surface 32. When the base 28 is pressed against the surface 32, the cement therebetween begins to spread. The rails 38 substantially prevent the bonding material from escaping across the mesial edge 40 and the distal edge 42 of the base 28. Consequently, the cement tends to flow occlusal-gingivally and excess cement escapes at the occlusal edge 56 and the gingival edge 54 of the base 28 due to the channels formed between the posts 44.

In the illustrated embodiment, the combinative post/rail benefits are achieved. In addition to providing a bonding surface with increased resistance to shear associated with mastication, the side portions 46 of the posts 44 are oriented to facilitate the occlusal-gingival flow of the cement during positioning on the tooth 34. As the base 28 is pressed against the surface 32, the bonding material flows between and about the posts 44 before the excess escapes. Air pockets are less likely to remain than in a base constructed according to the prior art as a result of the posts 44 and the spaces therebetween which provide a direct path for the air to escape. For example, if the posts 44 were oriented so that side portions 46 were parallel to the edges of the base 28, the bonding material might flow through occlusal-gingival channels between the posts 44 and leave air pockets in mesio-distal channels.

Although in FIGS. 2 and 4 the orthodontic appliance base is shown as an integral portion of an orthodontic bracket, it is to be understood that the base could be used with other orthodontic appliances. For example, the base may be formed as a separate pad and welded or brazed to a further orthodontic appliance.

Although the present invention has been described with respect to specific embodiments thereof, various changes and modifications may be suggested to one skilled in the art and it is intended that the present invention encompass such changes and modifications as fall within the scope of the appended claims.

What is claimed is:

1. An orthodontic appliance attachable to a patient's tooth and having a central, occlusally-gingivally extending axis, comprising:

a base having mesial, distal, occlusal, and gingival edges and a bottom, said mesial and distal edges each comprising a substantially planar debonding surface with each said debonding surface being inclined outwardly from said bottom relative to said central, occlusally-gingivally extending axis to define a space for positioning opposing portions of a debonding tool under opposing portions of said base prior to exerting a debonding force on said base.

2. An orthodontic appliance, as claimed in claim 1, further comprising:

a rail projecting from each of said mesial and distal edges and comprising a portion of said debonding surfaces.

3. An orthodontic appliance, as claimed in claim 2, wherein:

said base comprises an upper surface and said rails define a portion of said bottom, and wherein said rails project a greater distance from said upper surface than all remaining portions of said bottom between said rails.

* * * * *